United States Patent

Nicholson et al.

[11] 4,265,791
[45] May 5, 1981

[54] NOVEL PHOSPHORIC ACID

[75] Inventors: Richard R. Nicholson; Ray E. Smith; Jayendra G. Shukla, all of Ann Arbor, Mich.

[73] Assignee: Velsicol Chemical Corporation, Chicago, Ill.

[21] Appl. No.: 101,323

[22] Filed: Dec. 6, 1979

Related U.S. Application Data

[62] Division of Ser. No. 939,629, Sep. 5, 1978, Pat. No. 4,205,022.

[51] Int. Cl.³ ............................................. C09K 3/28
[52] U.S. Cl. ................................... 252/8.1; 106/18.19; 106/18.21; 260/29.4 R; 260/45.8 NT
[58] Field of Search ................. 260/29.4 R, 928, 953, 260/45.8 NT; 106/18.18, 18.21, 18.19; 252/8.1, 606, 607

[56] References Cited

U.S. PATENT DOCUMENTS

| | | | |
|---|---|---|---|
| 2,472,335 | 6/1949 | McLean et al. | 260/928 |
| 2,583,549 | 1/1952 | Daul et al. | 260/928 |
| 3,784,592 | 1/1974 | Leonard | 260/953 |
| 3,832,316 | 8/1974 | Juneja | 260/29.4 R |
| 4,013,599 | 3/1977 | Strauss et al. | 260/29.4 R |
| 4,099,975 | 7/1978 | Albright | 106/18.18 |
| 4,133,846 | 1/1979 | Albright | 260/928 |

*Primary Examiner*—Allan Lieberman
*Attorney, Agent, or Firm*—Dietmar H. Olesch; Robert J. Schwarz

[57] ABSTRACT

A compound of the formula

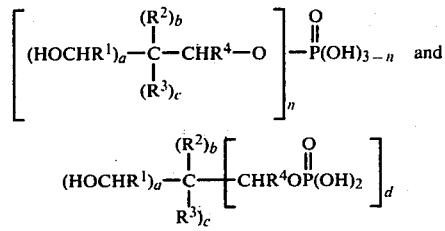

wherein a, b, c, d, and n are integers; a is from 1 to 3; b and c are independently selected from the group consisting of 0 and 1; d and n are independently selected from the group consisting of 1 and 2; $R^1$ and $R^4$ are independently selected from the group consisting of hydrogen, alkyl of 1 to 4 carbon atoms and haloalkyl of 1 to 4 carbon atoms and 1 to 2 halogen atoms; and $R^2$ and $R^3$ are independently selected from the group consisting of haloalkyl containing 1 to about 4 carbon atoms and 1 to about 2 halogen atoms selected from the group consisting of chlorine, bromine, and mixtures thereof.

The use of this compound with specified amounts of a certain methylated methylol melamine and water allows one to produce an intumescent composition which is substantially superior to prior art intumescent compositions.

5 Claims, No Drawings

NOVEL PHOSPHORIC ACID

This is a division of application Ser. No. 939,629, filed Sept. 5, 1978, now U.S. Pat. No. 4,205,022, issued May 27, 1980.

BRIEF SUMMARY OF INVENTION

A novel phosphoric acid which, when combined with methylated methylol melamine and water, produces a new and superior intumescent composition.

DETAILED DESCRIPTION

It is difficult to impart durable flame retardance to a wood substrate. Wood substrates present a flameproofing problem which is materially different from that presented by fibrous hydrophilic organic substrates. According to U.S. Pat. No. 2,927,050, in the latter substrate "... substantially independent fibers are tangled together, leaving interstices capable of being filled by an aqueous medium by capillary action between all of their surfaces. The individual fibers contain a relatively small amount of cellulose, and the materials composed of them have a relatively low ignition temperature." In wood substrates, however, "... the cellulosic fibers are bonded together to form a relatively impenetrable block susceptible to little capillary action. A piece of wood has small surface area in relation to the amount of surface volume it contains and has a relatively high ignition temperature." Because of these factors, "... a flameproofing agent which flameproofs fibrous hydrophilic organic materials is not likely to flameproof wood because its capacity to inhibit burning is likely to be destroyed by the time it is heated to the ignition temperature of the wood and/or because of the difficulty of causing a non-volatile substance to penetrate into the volume of a block of wood."

Impregnation of a wood substrate with a fire-retardant is known in the art. U.S. Pat. No. 3,398,019 teaches that this method must be used to impart a satisfactory degree of flame retardancy to wood fiber insulation, stating that "as far as is known only by the use of a chemical retardant which impregnates the board can a commerically acceptable building material be produced which is capable of securing a nonflammable rating." U.S. Pat. No. 4,049,849 teaches that this method, although well known, presents several substantial problems. According to this patent, the use of a wood substrate impregnated with a fire-retardant salt is restricted to low humidity applications "... due to the water solubility and hygroscopicity of most known fire retardant salts." Thus, "... if an ammonium phosphate-impregnated wood substrate is exposed to high (greater than 90 percent) humidity at ambient temperature, in approximately 3 days the fire retardant impregnant (salt) will leach therefrom ... The salt will absorb sufficient water vapor to enable it to migrate to the wood substrate surface. Not only does this leaching deplete the salt content of the wood substrate, rendering it less fire resistant, but it also severely disfigures the wood substrate's surface ..."

Those in the art have attempted to impart durable flame retardance to wood substrates by applying intumescent compositions to them. Many intumescent compositions have been tested; U.S. Pat. No. 3,668,121 correctly states that only a few of these compositions are of any value. Many of them produce excessive smoke and/or toxic gaseous pyrolysis products. According to U.S. Pat. No. 3,769,074, most of these prior art intumescent compositions are "... characterized by the disadvantages of high cost, low spreading rate, relatively poor efficiency, and poor weatherability." U.S. Pat. No. 3,513,144 teaches that prior art intumescent coating compositions "... exhibit the distinct disadvantage of either or both failing to maintain a coating film which will withstand repeated scrubbing or washing and thus exhibit wet abrasion resistant properties and/or failing to perform their intended function, that is, to intumesce, and thus fire retard after repeated scrubbing or washing." U.S. Pat. No. 3,535,130 teaches that "... conventional intumescent paints are usually sensitive to attack by water ..." U.S. Pat. No. 3,654,190 discloses that prior art intumescent compositions are water permeable and tend to degrade when exposed to moist environments.

U.S. Pat. No. 3,513,144 discloses that the problems presented by the prior art intumescent compositions cannot be solved merely by replacing the water soluble flame retardant agents they contain with water insoluble additives, for such substitutions does not necessarily increase the wet abrasion resistance properties of the compositions. Furthermore, such a substitution will present a new set of problems if the water insoluble additive must be dissolved in an organic solvent; for many dangers are created by the use of the common organic solvents. Toluene, for example, is a fire hazard and an explosion hazard when exposed to heat and flame; and it emits toxic fumes. Methylene chloride is very dangerous to the eyes. Benzene is highly flammable, causes leukemia, and it is a known carcinogen. Acetone is a fire hazard when exposed to either heat or flame. Methanol possesses narcotic properties and exerts a toxic effect upon the nervous system; once it is absorbed into the body, it is eliminated very slowly and, thus, is a cumulative poison. The use of almost any of the common organic solvents will present some fire hazard or explosion hazard or disaster hazard and/or cause some toxicological problem.

Other prior art considered by applicants during the preparation of this application include Japan Kokai No. 75,116,346 (preparation of neopentyl glycol phosphate), U.S. Pat. No. 3,445,547 (preparation of bis [bis(hydroxymethyl)butyl] hydrogen phosphate), U.S. Pat. No. 2,676,162 (an intumescent coating for wood containing organic solvent, methylated methylol melamine, the reaction product of ammonia and phosphoryl chloride, and a film-forming condensation product), U.S. Pat. No. 3,449,161 (fire-retardancy can be incorporated into paint compositions usin organo-phosphorus amides), U.S. Pat. No. 3,635,970 (melamine phosphate is especially useful in intumescent paint compositions), U.S. Pat. No. 4,026,810 (an intumescent flame retardant prepared by reacting, e.g., phosphoric oxide, phosphoric acid, pentaerythritol, and melamine and thereafter curing the reaction product by heating to evolve gaseous products), U.S. Pat. No. 2,582,961 (an aqueous flame retardant for cellulosic fiber containing, e.g., methylated methylol melamine, methylol dicyandiamide, and an oxygen-containing acid of phosphorus), U.S. Pat. No. 2,661,342 (flameproofing of cellulosic materials with a resinous aminoplast condensation product such as melamine and a water-soluble nitrogen- and phosphorus-containing product), U.S. Pat. No. 3,023,176 (a water-soluble hardenable condensation product which is prepared by reacting a methylol compound of the aminotriazine group, an aliphatic compound containing a chain of at least 7 carbon atoms and a reactive hydrogen bound to a hetero atom, and a compound that is capable of introducing atomic groupings that raise the hydrophilicity in a non-ionic manner), U.S. Pat. No. 3,101,278 (methylol-phosphorus polymers which have nitrogen atoms incorporated into them are excellent flame retardants and are suitable for treating cellulosic materials), and U.S. Pat. No. 3,332,240 (an aqueous solution for flameproofing cotton fiber containing a salt of hydroxylamine and melamine resin).

Applicants have discovered a novel compound which, when combined with a cyclic nirogen compound and water, forms an intumescent coating which is substantially superior to the intumescent coatings of the prior art. In accordance with this invention, there is provided a compound selected from the group consisting of

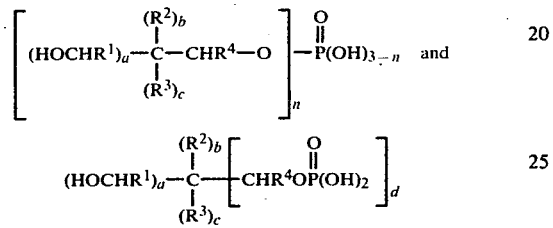

wherein a, b, c, d, and n are integers; a is from 1 to 3; b and c are independently selected from the group consisting of 0 and 1; d and n are independently selected from the group consisting of 1 and 2; $R^1$ and $R^4$ are independently selected from the group consisting of hydrogen, alkyl of 1 to 4 carbon atoms and haloalkyl of 1 to 4 carbon atoms and 1 to 2 halogen atoms; and $R^2$ and $R^3$ are independently selected from the group consisting of haloalkyl containing 1 to about 4 carbon atoms and 1 to about 2 halogen atoms selected from the group consisting of chlorine, bromine, and mixtures thereof.

In a preferred embodiment, the compound of this invention is

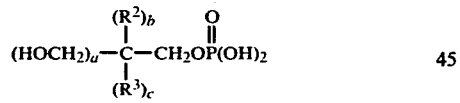

By way of illustration and not limitation, some of the compounds within the scope of this invention include, e.g., 2,2-bis(hydroxymethyl)-3-bromo-1-propyl phosphoric acid, 2,2-bis (hydroxymethyl)-3-chloro-1-propyl phosphoric acid, 2,2-bis(hydroxymethyl) propyl-1,3-diphosphoric acid, bis[2,2-bis(bromomethyl)-3-hydroxy-1-propyl] phosphoric acid, 2,2-bis(hydroxymethyl-5-bromo-1-pentyl phosphoric acid, 2,2-bis(hydroxymethyl)-4-bromo-1-butyl phosphoric acid, 2,2-bis(hydroxymethyl)-4-chloro-1-butyl phosphoric acid, 2,2-bis(bromomethyl)-3-hydroxy-1-propyl phosphoric acid, 2,2-bis(chloromethyl)-3-hydroxy-1-propyl phosphoric acid, 2,2-bis(bromoethyl)-3-hydroxy-1-propyl phosphoric acid, 2,2-bis(chloroethyl)-3-hydroxy-1-propyl phosphoric acid, bis[2,2-bis(chloroethyl)-3-hydroxy-1-propyl] phosphoric acid, bis [2,2-bis(chloromethyl)-3-hydroxy-1-hydroxy] phosphoric acid, bis [2,2-bis(bromoethyl)-3-hydroxy-1-propyl] phosphoric acid, 2-(hydroxymethyl)-2-bromomethyl-propyl-1,3-diphosphoric acid, 2-hydroxyethyl-2-bromomethyl-propyl 1,3-diphosphoric acid, 3,3 bis(bromomethyl)-4-hydroxy-2-pentyl phosphoric acid, and the like.

Some of the compounds of this invention may be prepared in accordance with the following reaction scheme:

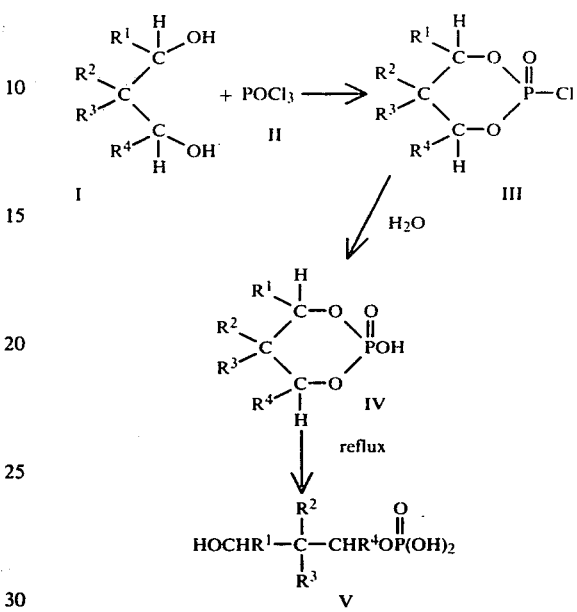

In this reaction, at least one mole of phosphoryl chloride (identified as reactant "II") is reacted with each mole of diol (identified as reactant "I") at a temperature of from about 25 to about 130 degrees centigrade for at least about 60 minutes until the theoretical amount of hydrochloric acid (two moles per mole of phosphoryl chloride) has been generated. It is preferred that the reaction between I and II be conducted at a temperature of from about 30 to about 100 degrees centigrade for at least about 240 minutes. It is most preferred that this reaction be conducted at a temperature of from about 40 to about 90 degrees centigrade. This reaction is generally conducted at atmospheric pressure; but subatmospheric and superatmospheric pressures may also be used.

The chlorophosphate intermediate (identified as "III") is reacted with at least two moles of water per mole of chlorophosphate for at least 30 minutes under conditions sufficiently severe to cause the reaction mixture to reflux; additional hydrochloric acid or hydrobromic acid may be added to the reaction mixture to increase the rate of ester cleavage. When the reaction is conducted at atmospheric pressure, a reaction temperature of from about 95 to about 110 degrees centigrade is used. It is preferred to utilize at least three moles of water for each mole of reactant III and conduct the reaction for at least about 60 /minutes. It is more preferred to use about 10 moles of water per mole of chlorophosphate reactant. This reaction is generally conducted at atmospheric pressure; but a portion of it or all of it may be conducted at superatmospheric pressure.

The compounds of this invention may be prepared by reacting precursors containing appropriate alcohol functionalities with phosphorus oxychloride and hydrolyzing the chlorophosphate or phosphate ester so produced.

The compound of this invention possesses some unique properties. When it is combined with both a certain cyclic nitrogen compound and water, one obtains an intumescent coating composition which is substantially superior to the intumescent coating compositions of the prior art; each of the components of this composition is water soluble.

It is preferred that the intumescent composition of this invention contains from about 8 to about 55 percent (by weight) of the acyclic compound of this invention, although it is most preferred that it contain from about 20 to about 45 percent (by weight) of said compound.

The intumescent coating composition of this invention contains a cyclic nitrogen compound. It is preferred that this composition contain about 10 to about 70 percent (by weight) of said cyclic nitrogen compound. As used in this specification, the term "percent" refers to a weight percent; it is the ratio of the weight of the component involved divided by the combined weights of all the components involved times 100.

The cyclic nitrogen compound used in the intumescent coating composition of this invention is described by the formula

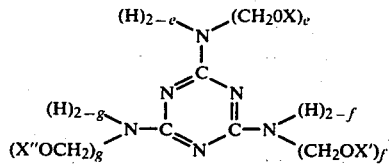

wherein e, f, and g are integers selected from the group consisting of 1 and 2, e plus f plus g equal about 3 to 6, and X, X', and X" are independently selected from the group consisting of hydrogen and —$CH_3$. It is preferred that at least one of said X, X', and X" groups be —$CH_3$. This cyclic nitrogen compound may be prepared by reacting at least three moles of formaldehyde per mole of melamine and then etherifying the methylol groups by reaction of the methylol melamine with methanol in the presence of an acid catalyst.

In the more preferred cyclic nitrogen compound used in the intumescent composition of this invention, at least about two of said X, X', and X" groups are —$CH_3$. In the most preferred embodiment at least three of said X, X', and X" groups are —$CH_3$.

The intumescent composition of this invention contains water. In a preferred embodiment, said composition contains from about 20 to about 40 percent (by weight) of water. In a more preferred embodiment, the composition contains from about 25 to about 35 percent of water.

The intumescent composition of this invention may be prepared by means known to the art. One may, e.g., mix in a dry state the acyclic compound of this invention with the cyclic nitrogen compound and then add the specified amount of water to the mixture. It is preferred, however, to mix solutions of said compounds together; the concentrations of such solutions are such that, after they are mixed together, the intumescent composition which results contains the specified amount of water, cyclic nitrogen compound, and acyclic compound. Thus, for example, one may mix an aqueous solution containing from about 50 to about 98 percent (by combined weight of water and cyclic nitrogen compound) of said cyclic nitrogen compound with an aqueous solution containing from about 30 to about 90 percent (by combined weight of water and acyclic compound) of said acyclic compound. In one preferred embodiment, an aqueous solution containing about 80 percent (by weight) of said cyclic nitrogen compound is mixed with an aqueous solution containing about 60 percent (by weight) of said acyclic compound.

Generally, the components of the intumescent composition of this invention are mixed together for at least about 60 seconds, although longer and shorter mixing times may be used.

The intumescent composition of this invention should be applied to a wood substrate within about 240 minutes of the time it is prepared. Although it is useful for most wood substrates, it is especially useful for imparting durable flame retardancy to a plywood substrate.

Plywood is a material made by bonding wood together with an adhesive. The layers are usually veneer; they are generally no greater than about 0.1875" thick for hardwood plywood and 0.1667" thick for softwood plywood. The successive layers (plies) have their grains at a definite angle to each other, usually 90 degrees.

The intumescent composition of this invention may be advantageously utilized with any of the plywood substrates well known to the art. It may be applied to the substrate by any method known to the art such as, e.g., by spraying, brushing, or coating the composition onto the plywood. It is preferred that the "dry solids add on" of the intumescent composition of this invention be from about 3 to about 15 grams per square foot of the plywood surface treated. The "add on" is determined by weighing the plywood substrate before and immediately afer it is treated. The percent of the solids in the composition applied times this difference is the number of grams of dry solids applied; the number of grams of dry solids applied divided by the number of square feet treated is the "add on" referred to in this specification. One coat of the intumescent compositon of this invention may be applied; it is preferred, however, to apply two or more coats.

After the composition of this invention is applied to the wood substrate, it is dried. It may be air dried, in which case up to about 30 hours should be allowed for it to dry. It may be dried by techniques well known to those skilled in the art. If heat is applied to the treated substrate, it is preferred to use a temperature of from about 70 to about 170 degrees centigrade for from about 1 to about 20 minutes. It is more preferred to dry the treated substrate at a temperature of from about 95 to about 110 degrees centigrade for from about 3 to about 10 minutes.

The following examples illustrate the claimed invention and are not to be deemed limitative thereof. Unless otherwise specified, all parts are by weight, all temperatures are in degrees centigrade, all weights are expressed in grams, and all volumes are expressed in milliliters.

EXAMPLE 1

2,2-bis(bromomethyl)-3-hydroxy-1-propyl phosphoric acid

Five thousand two hundred and forty grams (20.0 moles) of dibromoneopentyl glycol and 3,070 grams of phosphoryl chloride were placed in a 12-liter round-bottom flask equipped with a stirrer, heating mantle, and condenser. The reaction mixture was consecutively maintained at ambient temperature fo 30 minutes, a temperature of 40–45 degrees centigrade for 60 minutes, a temperature of 50 degrees centigrade for 60 minutes, a temperature of 70 degrees centigrade for 60 minutes, a temperature of 90 degrees centigrade for 120 minutes, and a temperature of 110 degrees centigrade (under aspirator vacuum) for 60 minutes. The reaction mixture was allowed to stand overnight.

Two hundred grams (0.58 moles) of 2-chloro-5,5-bis(-bromomethyl)-2-oxo-1,3,2-dioxaphosphorinane produced in substantial accordance with the procedure described in this example and 80 grams of water were charged to a one-liter flask and heated to reflux for 240 minutes at a temperature of about 100 degrees centigrade; the reaction was conducted at atmospheric pressure. Thereafter the hydrochloric acid generated in situ by this reaction was removed by subjecting the reaction mixture to a reduced pressure of 20 millimeters of mercury absolute and a temperature of up to about 100 degrees centigrade for 120 minutes. A white solid material was obtained. Analyses indicated that it contained 45.74 percent (by weight) of bromine and had an acid number of 302; this material should, according to theory, contain 46.7 percent (by weight) of bromine and have an acid number of 328.

EXAMPLE 2

Sixty parts of an 80 percent aqueous solution of Aerotex Resin M-3 ®, a methylated trimethylol melamine compound available from the American Cyanamide Corporation, were mixed with 40 parts of a 60 percent aqueous solution of the compound of Example 1. Two coats of this formulation were brushed onto a lauan plywood sample (which contained a groove and was 24" long, 3,5" wide, and 0.1875" thick) to a dry solids add on of 10 grams per square foot. The coated sample was then dried at a temperature of about 100 degrees centigrade for about 5 minutes. Thereafter the sample was subjected to a two-foot tunnel test to determine its flame spread rate; this test was conducted in substantial accordance with the procedure described in an article entitled "Two-Foot Tunnel Test," *Journal of Paint Technology*, Vol. 11, No. 565, February 1972, pp. 43–47; however the panels were not conditioned as described in this article.

The two-foot tunnel test is a small scale test designed to simulate the UL Steiner 25-foot tunnel test described by ASTM E84-68. In the former test, the two-foot tunnel was inclined 28 degrees from the horizontal and utilized approximately 96 square inches of test surface. The test specimen was mounted on an angle iron frame in such a way that the surface to be evaluated formed the ceiling of the tunnel. A standard Meeker burner was placed at the lower end of the tunnel, and the specimen was subjected to the flame from this burner for five minutes; during the first four minutes, the length of the advance of the flame front up the inclined panel was recorded at 15 second intervals. The flame lengths were measured by observing the flame front advance through a calibrated window located on the side of the tunnel. The tunnel was calibrated prior to specimen testing by determining the difference in flame lengths of a specimen of asbestos cement board and a specimen of red oak; this difference, by introduction of a constant K, was given a flame spread rating ("FSR") of 100. The flame spread rate calculation was made in accordance with the formula $F.S.R. = (L_n - L_a)K$ wherein F.S.R. was the flame spread rating, $L_n$ was the observed flame of the specimen tested, $L_a$ was the flame for asbestos cement board, $L_o$ was the observed flame length for the red oak sample, and $K = 100/L_o - L_a$.

The samples were weighed both before and after being tested in the two-foot tunnel, and the percent weight loss due to combustion of the sample was determined.

The coated plywood sample of this example had a flame spread rating of 20 and lost about 6 percent of its weight.

EXAMPLE 3

The procedure of Example 2 was repeated with the exception that 30 parts of the 80 percent trimethylated trimethylol melamine solution and 70 parts of the 60 percent solution of the compound of Example 1 were combined to yield a formulation which was applied to the lauan plywood sample to a dry solids add on of 10 grams per square foot. The flame spread rating was 30, and the percent weight loss was about 6.5 percent.

EXAMPLE 4

2,2-bis(hydroxymethyl)propyl-1,3-diphosphoric acid

One hundred eithty-three grams of 3,9-dichloro-2,4,8,10-tetraoxa-3,9-diphosphaspiro-(5,5)undecane-3,9-dioxide were mixed with 200 milliliters of deionized water and heated gently to reflux. An exothermic reaction occurred; frothing was noticed as the temperature of the reaction mixture approached 100 degrees centigrade. A clear solution was obtained during a 30 minute reflux. Hydrochloric acid was removed at reduced pressure until terminal conditions (at 100 degrees centigrade and 15 millimeters of pressure) were reached. One hundred and seven grams of deionized water were added, resulting in a 65 percent solution. Analysis of this solution indicated that it had an acid number of 444. Fifty parts of this solution were mixed with 50 parts of the 80 percent trimethylated trimethylol melamine solution to yield a formulation which was applied to the lauan plywood sample to a dry solids add on of 8 grams per square foot. The flame spread rating was 30, and the percent weight loss was about 6.1 percent.

EXAMPLES 5 and 6

Eighty-six grams of monobromopentaerythritol and 66 grams of phosphorus oxychloride were maintained at a reaction temperature of 40–45 degrees centigrade for 30 minutes while being stirred. The reaction mixture was then heated to 50 degrees centigrade and held there for 60 minutes. Then the mixture was heated to 70 degrees centigrade for 60 minutes and hydrolyzed in 60 milliliters of 6 molar hydrochloric acid. After 90 minutes of refluxing, the hydrochloric acid was removed under reduced pressure to terminal conditions of 100 degrees centigrade and 15 millimeters of mercury. Eighty grams of water were added to the reaction mixture resulting in a 57 percent solution of 2,2-bis(hydroxymethyl)-3-bromo-1-propyl phosphoric acid; this solution contained 16.2 percent bromine. In Example 5 forty parts of this solution were mixed with 60 parts of the 80 percent aqueous solution of methylated trimethylol malamine; in Example 6, 50 parts of this solution were mixed with 50 parts of the 80 percent aqueous solution of methylated trimethylol melamine. In both examples, the formulation was applied to the lauan plywood sample to a dry solids add on of 9 grams per square foot.

The flame spread rating of the plywood sample of Example 5 was 35, and its percent weight loss was about 7.5. The flame spread rating of the plywood sample of Example 6 was 35, and its percent weight loss was about 7.0.

COMPARATIVE EXAMPLES 7 AND 8

The compound prepared in accordance with the procedure of Example 1 was neutralized with a 28 percent solution of ammonium hydroxide until its pH was about 4.0; thereafter a 60 percent aqueous solution of this partially neutralized acid was prepared.

Formulations containing the 80 percent trimethylated trimethylol melamine solution and the 60 percent solution of the partially neutralized acid were prepared. In Example 7, 60 parts of the former component and 40 parts of the latter component were combined to yield a formulation which was applied in two coats to a dry solids add on of about 8.5 grams per square foot. In Example 8, 30 parts of the former component and 70 parts of the latter component were combined to yield a formulation which was applied in two coats to a dry solids add on of about 7.5 grams per square foot. The materials and procedures described in Example 2 were utilized.

The coated plywood sample of Example 7 had a flame spread rating of 55 and lost 10 percent of its weight. The coated plywood sample of Example 8 had a flame spread rating of 95 and lost 13 percent of its weight. Both of these samples generated a substantial amount of smoke during combustion.

COMPARATIVE EXAMPLE 9

Fifty parts of trimethylated trimethylol melamine were mixed with 50 parts of an 85 percent aqueous solution of phosphoric acid to yield a formulation which was applied to a dry solids add on of 8.0 grams per square foot. A very brittle film which exhibited blistering on its surface was formed.

The above examples have been described for the purpose of illustration, not limitation. Many other modifications will suggest themselves to those skilled in the art; they are intended to be comprehended within the scope of this invention.

The embodiments of this invention in which an exclusive property or privilege is claimed are as follows:

1. An intumescent composition consisting essentially of from about 8 to about 55 percent by weight of a compound selected from the group consisting of:

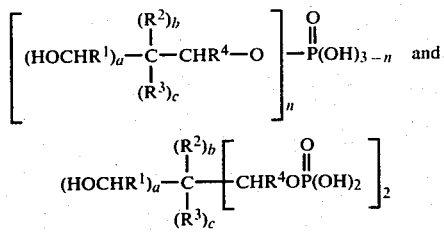

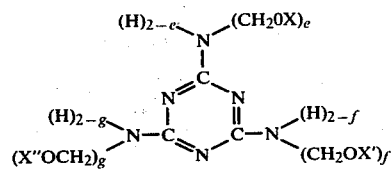

wherein a, b, c, and n are integers; a is from 1 to 3; b and c are independently selected from the group consisting of 0 and 1; n is selected from the group consisting of 1 and 2; $R^1$ and $R^4$ are independently selected from the group consisting of hydrogen, alkyl of 1 to 4 carbon atoms and haloalkyl of 1 to 4 carbon atoms and 1 to 2 halogen atoms; and $R^2$ and $R^3$ are independently selected from the group consisting of haloalkyl containing 1 to about 4 carbon atoms and 1 to about 2 halogen atoms selected from the group consisting of chlorine, bromine, and mixtures thereof; from about 20 to about 40 percent by weight of water, and from about 10 to about 70 percent by weight of a cyclic nitrogen compound of the formula $$(H)_{2-e}\phantom{X}N\phantom{X}(CH_2OX)_e$$

$$(H)_{2-g}\phantom{X}N-C\phantom{XX}C-N\phantom{X}(H)_{2-f}$$
$$(X''OCH_2)_g\phantom{XXXX}N\phantom{XXXX}(CH_2OX')_f$$

wherein e, f, and g are integers selected from the group consisting of 1 and 2, e plus f plus g equal about 3 to 6, and X, X', and X" are independently selected from the group consisting of hydrogen and —$CH_3$.

2. The composition of claim 1, wherein at least one of said X, X', and X" groups is —$CH_3$.

3. The intumescent composition of claim 2, wherein said composition contains from about 25 to about 35 percent by weight of water.

4. The intumescent composition of claim 3, wherein X, X', and X" are —$CH_3$.

5. The intumescent composition of claim 4, wherein said composition contains from about 20 to about 45 percent by weight of the phosphorous compound of claim 1, from about 25 to about 35 percent by weight of water, and from about 20 to about 50 percent by weight of the cyclic nitrogen compound of claim 1.

* * * * *